(12) United States Patent
Wilson

(10) Patent No.: US 8,109,884 B2
(45) Date of Patent: Feb. 7, 2012

(54) DYNAMIC METABOLISM MONITORING SYSTEM

(76) Inventor: Kitchener Clark Wilson, Santa Barbara, CA (US)

(*) Notice: Subject to any disclaimer, the term of this patent is extended or adjusted under 35 U.S.C. 154(b) by 1201 days.

(21) Appl. No.: 11/525,803

(22) Filed: Sep. 22, 2006

(65) Prior Publication Data

US 2007/0073182 A1    Mar. 29, 2007

Related U.S. Application Data

(60) Provisional application No. 60/719,883, filed on Sep. 23, 2005.

(51) Int. Cl.
*A61B 5/08* (2006.01)
(52) U.S. Cl. ......... 600/529; 600/531; 600/532; 600/538
(58) Field of Classification Search .................. 600/529, 600/531, 532, 538, 543
See application file for complete search history.

(56) References Cited

U.S. PATENT DOCUMENTS

2003/0208133 A1* 11/2003 Mault ........................... 600/532
2006/0184057 A1*  8/2006 Flanagan ...................... 600/531

* cited by examiner

*Primary Examiner* — Patricia Mallari
*Assistant Examiner* — Christian Jang

(57) ABSTRACT

A metabolism monitoring system, data analyzer, and method is disclosed for processing data to very quickly estimate metabolic parameters. The analyzer of the invention uses a dynamic observer state estimator to estimate the parameters and tracks their values as they change with alterations in the patient metabolism or testing conditions. The state estimator does not use the conventional steady state solutions. The observer predicts the patient consumption of oxygen and exhalation of carbon dioxide at a subsequent point in time, corrects these values using measurements of air flow rate and chamber levels of oxygen and carbon dioxide taken at that subsequent time, and repeats for the next time. The corrected values are used for estimation of the metabolic parameters.

14 Claims, 11 Drawing Sheets

FIG. 1: PRIOR ART

DYNAMIC METABOLISM MONITORING SYSTEM

RELATED APPLICATIONS

This application claims the benefit of U.S. Provisional Application Ser. No. 60/719,883 filed 23 Sep. 2005.

BACKGROUND OF THE INVENTION

1. Field of the Invention

The present invention relates generally to devices for measuring metabolic parameters. More particularly, the present invention relates to apparatus and methods to generate rapid estimates of these parameters.

2. General Background and State of the Art

Metabolic chambers based on open circuit spirometry are used to determine the metabolic parameters of a patient within it. With the obesity epidemic of current concern, such information is of particular interest for infants and young children as a noninvasive tool to evaluate their metabolic status and food requirements. Metabolic chambers are also used to monitor the metabolism of non-humans such as farm animals (cattle, pigs, . . . ) and laboratory test animals (rats, mice, monkeys, . . . ). To be effective clinically, the chambers need to produce metabolic parameters quickly and reliably.

A metabolic chamber can be a rigid structure made of solid plastic or glass walls, or a flexible structure like the plastic film canopy placed over patients. To generate the metabolic parameters, the chamber air is steadily removed while fresh air enters, and the removed air is sampled to determine the fractions of $CO_2$ and $O_2$ and the air removal flow rate. Metabolic parameters are determined by combining these in equations describing the steady state condition of the chamber. These results are not valid until steady state is achieved, and this is dependent on the volume of the chamber and the entry and removal flow rates. In typical chambers designed for infants, steady state can take as long as an hour and, since during this time the metabolism of the patient can be changing, steady state may never actually exist.

The ability to determine metabolic parameters quickly while the chamber is not at steady state is preferred and would make it possible to reduce the time the patient is in the chamber and to produce more accurate metabolic parameter values. There is a need to provide an apparatus and method to accomplish this.

Commercially available metabolism monitoring devices may not enclose the patient, but use a mouthpiece through which the patient breathes into a mixing chamber or a small chamber enclosing only the head (Deltatrac II by Datex-Ohmeda). Commercial devices (Deltatrac II) are also used to monitor intensive care patients lying under large canopies having volumes large enough to be affected by steady state equilibration and that can be improved using the invention described herein.

SUMMARY OF THE INVENTION

Accordingly, it is an object of the present invention to provide a dynamic method to produce accurate metabolic parameters while the chamber is not in steady state.

An additional object of the invention is to provide a chamber designed to optimize the dynamic metabolic parameter determination method.

It is yet another object of the invention to retro-fit existing chambers such that they are made compatible with the dynamic metabolic parameter determination method.

These and other objectives are achieved by the present invention, which, in a broad aspect, is a dynamic method of analyzing the metabolic chamber measurements in a manner that is independent of the steady state chamber condition, and that produces accurate metabolic parameter values many times faster than current steady state methods. The present invention also includes a chamber design to facilitate the dynamic metabolic parameter determination. The present invention also includes a design to retro-fit existing non-facilitated chambers.

Further objects and advantages of the present invention will become more apparent from the following description of the preferred embodiments which, taken in conjunction with the accompanying drawings, illustrate, by way of example, the principles of the invention.

DETAILED DESCRIPTION OF THE PREFERRED EMBODIMENTS OF THE INVENTION

Current metabolism monitoring devices are based on a simplistic steady state mathematical model of the chamber dynamics. Even small chambers enclosing infants can take as much as an hour to reach steady state, if it exists at all given normal changes in the patient's metabolism with activity. Means to eliminate this delay will greatly advance the clinical use of metabolic chambers.

Figure 1:
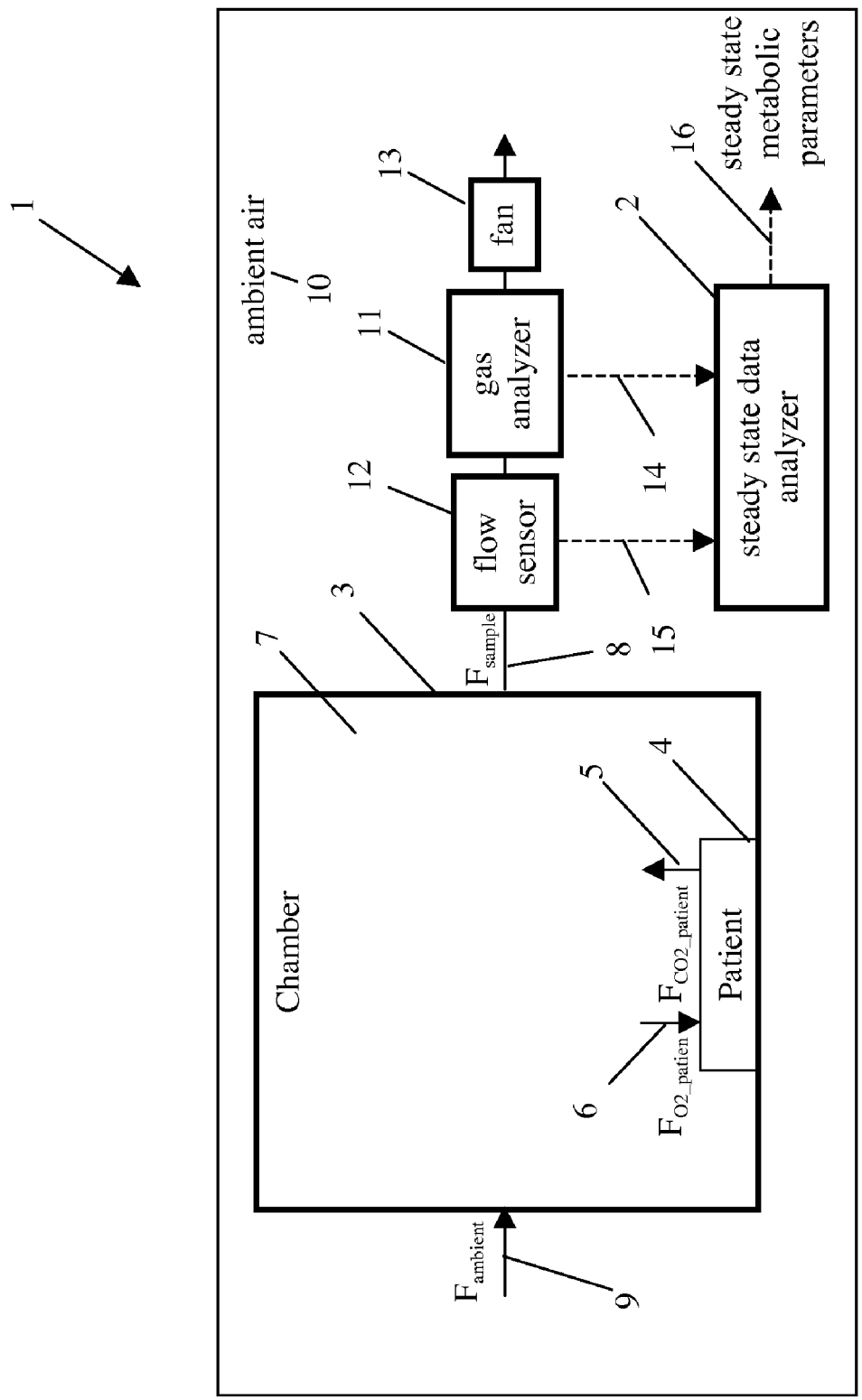
FIG. 1 is a schematic representation of a conventional metabolic chamber using steady state methods to estimate metabolic parameters.

FIG. 1 illustrates a conventional metabolic parameter estimation system 1 using a steady state data analyzer 2. The chamber 3 encloses a patient 4, a portion of a patient, or otherwise exchanges gas with a patient. The patient is a $F_{CO2\_patient}$ source 5 of carbon dioxide and a $F_{O2\_patient}$ sink 6 of oxygen. The gas 7 within the chamber is evacuated at rate $F_{sample}$ 8 for measurement and replaced 9 by $F_{ambient}$ inflow from ambient 10. The evacuated air 8 is analyzed 11 to determine the volume fraction of oxygen and carbon dioxide, temperature, humidity, pressure, and the gas outflow rate 8 is measured 15 by flow sensor 12. A fan or air pump 13 acts to move the air through the system.

The chamber 3 has volume $V_{chamber}$ after compensation for the patient 4 volume, and a fan (not shown) is included within the chamber to mix and uniformly distribute the chamber 3 gas contents 7. The data 14 from the gas analyzer 11 and the data 15 from the flow sensor 12 are allowed to reach a steady state (unchanging) equilibrium condition and then used to calculate steady state metabolic parameters 16 based on estimates of the patient's oxygen consumption rate 6, carbon dioxide generation rate 5, and gas outflow rate data 15.

Derivation of the Chamber Dynamic Mathematical Model

While the steady state chamber analyzer 2 is based on a steady state model of the chamber, the non-steady state dynamic chamber analyzer is based on a dynamic chamber model. The gas flow dynamics reflect the movement of oxygen, carbon dioxide and metabolically inert gases from ambient air through the chamber where it exchanges with the patient, and passes through a gas analyzer drawn by a fan or air pump. The gas analyzer determines the volumetric fractions of oxygen and carbon dioxide along with the pressure, temperature, flow rate, and humidity of the sampled chamber air. Temperature, pressure and humidity are used to correct the measured pressure to standard conditions.

To begin the mathematical model, the molar content of air within the chamber is described based on the flow in, flow out, and that provided by the patient as $$\dot{q}_{O2\_chamber} = \dot{q}_{O2\_ambient} - \dot{q}_{O2\_sample} - \dot{q}_{O2\_patient}$$

$$\dot{q}_{CO2\_chamber} = \dot{q}_{CO2\_ambient} - \dot{q}_{CO2\_sample} - \dot{q}_{CO2\_patient}$$

$$\dot{q}_{N2\_chamber} = \dot{q}_{N2\_ambient} - \dot{q}_{N2\_sample} \quad (1)$$

where $\dot{q}_x$ is the rate of change (moles/sec) of the molar quantity of x, $\dot{q}_{x\_ambient}$ is the flow rate into the chamber, $\dot{q}_{x\_sample}$ is the flow rate out of the chamber, $\dot{q}_{x\_patient}$ is the patient exchange flow rate, and $\dot{q}_{x\_chamber}$ the rate of change within the chamber. The symbol $N_2$ represents nitrogen and all other metabolically inert atmosphere constituents, like argon.

The ideal gas law states that $$PV = qRT$$

where P is the pressure (mmHg) of a gas mixture, V is the volume (liter) within which the gas mixture is constrained, q is the moles of gas molecules, R is the gas constant (62.363 mmHg-liter/mole-° K), and T the temperature (° K) of the gas. Taking the derivative of both sides and assuming the rates of change pressure and temperature are insignificant, $$P\dot{V} = \dot{q}RT$$

Since the rate of change of volume is the flow rate (liter/sec), F, $$PF = \dot{q}RT$$

and $$\dot{q} = \frac{P}{RT}F$$

For a given species x having volumetric fraction $f_x$, multiplying both sides by the fraction yields $$\dot{q}_x = \frac{PF}{RT}f_x$$

and, in particular, $$\dot{q}_{x\_sample} = \frac{P_{sample}F_{sample}}{RT_{sample}}f_{x\_sample} \quad (2)$$

$$\dot{q}_{x\_patient} = \frac{P_{sample}F_{x\_patient}}{RT_{sample}}$$

$$\dot{q}_{x\_ambient} = \frac{P_{ambient}F_{ambient}}{RT_{ambient}}f_{x\_ambient}$$

The species volumetric fraction in the sample is the same as that in the chamber and given by $$f_{x\_sample} = \frac{\dot{q}_{x\_chamber}}{\dot{q}_{O2\_chamber} + \dot{q}_{CO2\_chamber} + \dot{q}_{N2\_chamber}} \quad (3)$$

and the airflow from ambient into the chamber is driven by the pressure difference between the two:

$$F_{ambient} = \frac{P_{ambient} - P_{sample}}{\rho} \quad (4)$$

where ρ is the inlet orifice resistance to flow in mmHg per liter/sec that is determined experimentally given a chamber, or theoretically given a design.

Equation (4) states a flow sensor is not needed if the flow characteristics of the inlet orifice are known. In such a case the $F_{ambient}$ is determined from the ambient and chamber pressure measurements.

Equations (1-4) are sufficient to model and simulate the dynamics of the chamber given
  the ambient humidity-corrected pressure, temperature, species fractions;
  inlet flow resistance, chamber volume;
  the sample flow rate, temperature, and humidity-corrected pressure; and
  the patient oxygen and carbon dioxide net consumption and exhalation flow rates.

The integration of Equations (1) is performed numerically using any number of methods (e.g. Euler, Newton, Simpson, Huen, etc.).

Since the measurements are in terms of volumetric fractions rather than moles, it would be more useful to have the model in these terms. This process begins by taking the derivative of Equation (3) as $$\dot{f}_{x\_sample} = \frac{\dot{q}_{x\_chamber}(q_{O2\_chamber} + q_{CO2\_chamber} + q_{N2\_chamber}) -}{q_{x\_chamber}(\dot{q}_{O2\_chamber} + \dot{q}_{CO2\_chamber} + \dot{q}_{N2\_chamber})} \quad (5)$$

$$q_{O2\_chamber} + q_{CO2\_chamber} + q_{N2\_chamber} = \frac{P_{sample}V_{chamber}}{RT_{sample}} \quad (6)$$

$$q_{x\_chamber} = \frac{P_{sample}V_{chamber}}{RT_{sample}} f_{x\_sample}$$

$$f_{N2} = 1 - f_{O2} - f_{CO2} \quad (7)$$

Substituting Equations (1, 2, 6, 7) into Equation (5)

$$\dot{f}_{O2\_sample} = \frac{1}{V_{chamber}}[-(F^*_{ambient} - F_{O2\_patient} + F_{CO2\_patient})f_{O2\_sample} + \quad (8)$$

$$F^*_{ambient}f_{O2\_ambient} - F_{O2\_patient}]$$

$$\dot{f}_{CO2\_sample} = \frac{1}{V_{chamber}}[-(F^*_{ambient} - F_{O2\_patient} + F_{CO2\_patient})$$

$$f_{CO2\_sample} + F^*_{ambient}f_{CO2\_ambient} + F_{CO2\_patient}]$$

$$\dot{f}_{N2\_sample} = \frac{1}{V_{chamber}}[-(F^*_{ambient} - F_{O2\_patient} + F_{CO2\_patient})f_{N2\_sample} +$$

$$F^*_{ambient}f_{N2\_amabient}]$$

where $$F^*_{ambient} \equiv \frac{P_{ambient}T_{sample}}{P_{sample}T_{ambient}} F_{ambient}$$

Equations (8) clearly state the dynamics of the gas fractions are not directly dependent on the sample flow, but on the ambient flow. This makes sense since the flow of ambient directly changes the gas fraction while the sample flow does so only indirectly by lowering the chamber pressure and stimulating ambient flow.

At steady state the derivatives of Equations (8) are zero and, since at steady state $$F_{sample\_ss} = F^*_{ambient\_ss} - F_{O2\_patient\_ss} + F_{CO2\_patient\_ss} \quad (9)$$

then $$0 = -F_{sample\_ss}f_{O2\_sample\_ss} + F^*_{ambient\_ss}f_{O2\_ambient} - F_{O2\_patient\_ss}$$

$$0 = -F_{sample\_ss}f_{CO2\_sample\_ss} + F^*_{ambient\_ss} f_{CO2\_ambient} + F_{CO2\_patient\_ss}$$

$$0 = -F_{sample\_ss}f_{N2\_sample\_ss} + F^*_{ambient\_ss}f_{N2\_ambient}$$

These steady equations are solved as $$F^*_{ambient\_ss} = \frac{1 - f_{O2\_sample\_ss} - f_{CO2\_sample\_ss}}{f_{N2\_ambient}} F_{sample\_ss} \quad (10)$$

$$F_{O2\_patient\_ss} =$$

$$-\left(f_{O2\_sample\_ss} - \frac{1 - f_{O2-sample\_ss} - f_{CO2\_sample\_ss}}{f_{N2\_ambient}} f_{O2-ambient}\right)$$

$$F_{samplpe\_ss}$$

$$F_{CO2\_patient\_ss} =$$

$$\left(f_{CO2\_sample\_ss} - \frac{1 - f_{O2\_sample\_ss} - f_{CO2\_sample\_ss}}{f_{N2\_ambient}} f_{CO2\_ambient}\right)$$

$$F_{sample\_ss}$$

Variations of these steady state equations are commonly used in steady state open circuit metabolic devices. The so-called 'Haldane correction', in which the $N_2$ fractions come into play, is implicit in these equations.

It can be shown that the $N_2$ differential equation has no new information since the $N_2$ correction of Equation (7) is built into the oxygen and carbon dioxide fraction differentials. The complete dynamic model is then $$\dot{f}_{O2\_sample} = \quad (11)$$

$$\frac{1}{V_{chamber}}[-(F^*_{ambient} - F_{O2\_patient} + F_{CO2\_pateint})f_{O2\_sample} +$$

$$F^*_{ambient}f_{O2\_ambient} - F_{O2\_patient}]$$

$$\dot{f}_{CO2\_sample} = \frac{1}{V_{chamber}}[-(F^*_{ambient} - F_{O2\_patient} + F_{CO2\_pateint})$$

$$f_{CO2\_sample} + F^*_{ambient}f_{CO2\_ambient} - F_{CO2\_patient}]$$

where the $f_{O2\_sample}$, $f_{CO2\_sample}$, $P_{ambient}$, $P_{sample}$, $T_{ambient}$, $T_{sample}$, and $F_{ambient}$ are measured, and $F_{O2\_patient}$ and $F_{CO2\_patient}$ are to be determined and are the basis of metabolic parameter determinations. The chamber volume, $V_{chamber}$ is known or estimated by other means as discussed below.

Formation of a Dynamic Metabolic Parameter Analyzer

The general approach to using Equations (11) to dynamically estimate the flows $F_{O2\_patient}$ and $F_{CO2\_patient}$ is to create an observer or state estimator. These methods are based on generating a prediction of the unknowns and using these predictions to predict the measurements. The differences between the predicted and actual measurements are used to correct the unknown estimates dynamically with each new measurement. Say there exist, at time $t_i$, an estimate of the flows $F_{O2\_patient@i/i}$ and $F_{CO2\_patient@i/i}$, a mathematical model to predict what they will be at a future time $t_{i+1}$ providing $F_{O2\_patient@i+1/i}$ and $F_{O2\_patient@i+1/i}$, and a mathematical model to convert them into predictions of the anticipated data at time $t_{i+1}$, providing $f_{O2\_sample@i+1/i}$ and $f_{CO2\_sample@i+1/i}$. When actual data $f_{O2\_sample\_measured@i+1}$ and $f_{CO2\_sample\_measured@i+1}$ are available, they are used to correct and update the estimates as $$F_{O2\_patient@i+1/i+1} = F_{O2\_patient@i+1/i} + kF_{O2/O2}$$
$$(f_{O2\_sample\_measured@i+1} - f_{O2\_sample@i+1/i}) + kF_{O2/}$$
$$CO2(f_{CO2\_sample\_measured@i+1} - f_{CO2\_sample@i+1/i})$$

$$F_{CO2\_patient@i+1/i+1} = F_{CO2\_patient@i+1/i} + kF_{CO2/O2}$$
$$(f_{O2\_sample\_measured@i+1} - f_{O2\_sample@i+1/i}) +$$
$$kF_{CO2/CO2}(f_{CO2\_sample\_measured@i+1} -$$
$$f_{CO2\_sample@i+1/i})$$

$$f_{O2\_patient@i+1/i+1} = f_{O2\_patient@i+1/i} + kf_{O2/O2}$$
$$(f_{O2\_sample\_measured@i+1} - f_{O2\_sample@i+1/i}) + kf_{O2/}$$
$$CO2(f_{CO2\_sample\_measured@i+1} - f_{CO2\_sample@i+1/i})$$

$$f_{CO2\_patient@i+1/i+1} = f_{CO2\_patient@i+1/i} + kF_{CO2/O2}$$
$$(f_{O2\_sample\_measured@i+1} - f_{O2\_sample@i+1/i}) +$$
$$kF_{CO2/CO2}(f_{CO2\_sample\_measured@i+1} -$$
$$f_{CO2\_sample@i+1/i}) \quad (12)$$

The kf and kF correction gains are determined to make a best correction.

Figure 2:
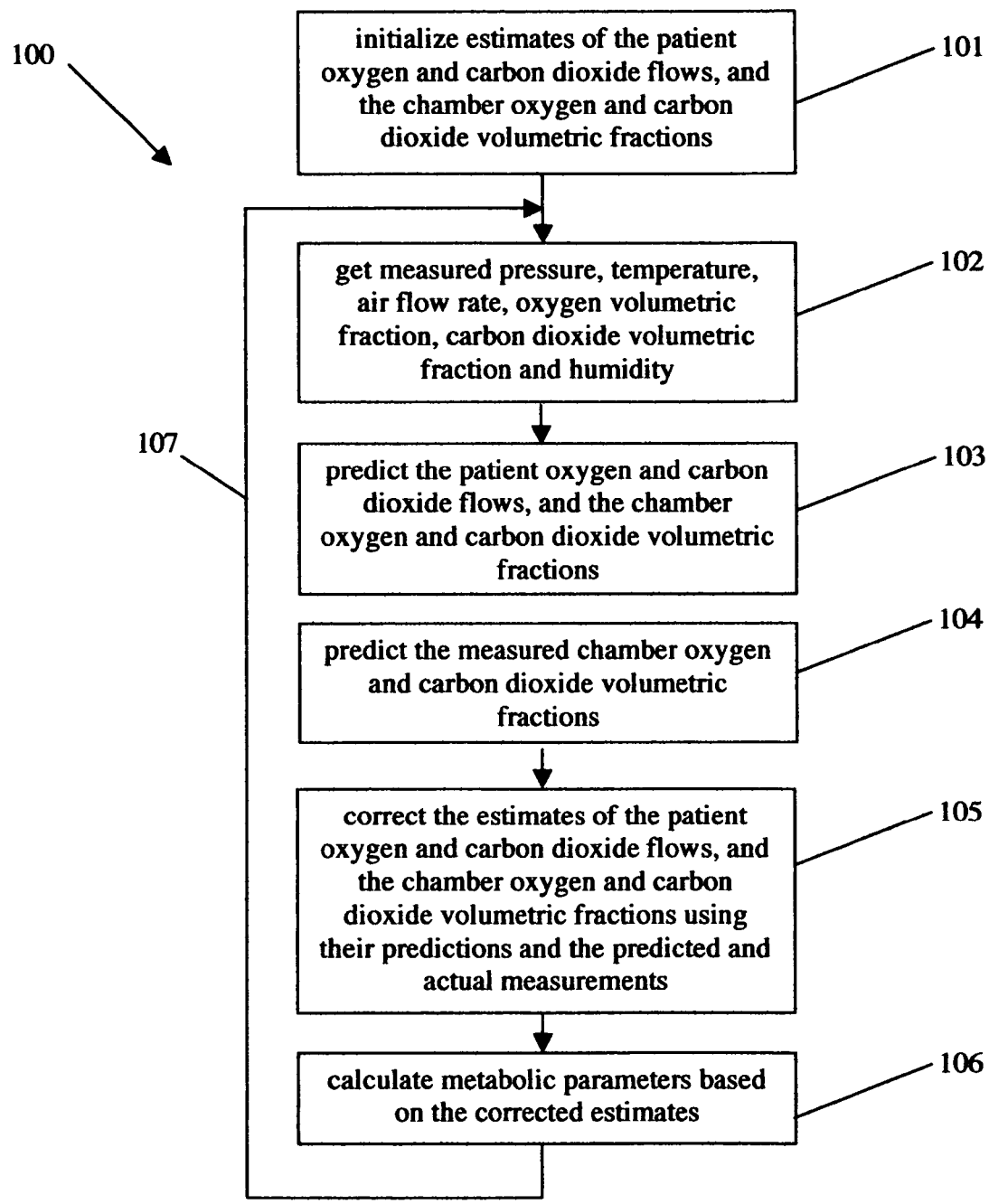
FIG. 2 is a flow diagram showing the stepwise operation of a dynamic metabolic parameter estimator.

For the purpose of designing an observer or state estimator, the equations representing the dynamic model of the metabolic chamber are lacking a description of the dynamics of the patient flow rates. Appending simple models of the $F_{O2\_patient}$ and $F_{CO2\_patient}$ dynamics, where their derivatives are considered Gaussian white random variables in the manner of stochastic modeling, provides the complete system model $$\dot{F}_{O2\_patient} = \delta_{FO2\_patient\_rate} \quad (13)$$

$$\dot{F}_{CO2\_patient} = \delta_{FCO2\_patient\_rate}$$

$$\dot{f}_{O2\_sample} = \frac{1}{V_{chamber}} [-(F^*_{ambient} - F_{O2\_patient} + F_{CO2\_patient}) f_{O2\_sample} + F^*_{ambient} f_{O2\_ambient} - F_{O2\_patient}]$$

$$\dot{f}_{CO2\_sample} = \frac{1}{V_{chamber}} [-(F^*_{ambient} - F_{O2\_patient} + F_{CO2\_patient}) f_{CO2\_sample} + F^*_{ambient} f_{CO2\_ambient} - F_{CO2\_patient}]$$

with measurements $$f_{O2\_sample\_measured} = f_{O2\_sample} + \delta_{fO2\_sample\_measurement}$$

$$f_{CO2\_sample\_measured} = f_{CO2\_sample} + \delta_{fCO2\_sample\_measurement} \quad (14)$$

where the $\delta_F$ terms are zero mean uncorrelated Gaussian random state noise variables having known standard deviations $\sigma_{FO2\_patient\_rate}$ and $\sigma_{FCO2\_patient\_rate}$, and the $\delta_f$ terms are Gaussian random measurement noise variables having known standard deviations $\sigma_{fO2\_sample\_measurement}$ and $\sigma_{fCO2\_sample\_measurement}$. These equations provide four coupled nonlinear time varying stochastic differential equations and are the basis for the observer state estimator. Defining the estimator state vector, $\underline{x}$ $$\underline{x}_i = \underline{x}(t_i) = [F_{O2\_patient@i} f_{O2\_sample@i} F_{CO2\_patient@i} f_{CO2\_sample@i}]^T$$

the dynamic estimator procedure 100, illustrated in FIG. 2, operates by initializing 101 the state values; receiving the chamber measurements 102; predicting 103 the state at the measurement time; predicting 104 the measurements using the predicted state value; correcting 105 the state value using the measurements and the predicted measurements; outputting 106 the dynamic metabolic parameters derived from the corrected state values; and waiting 107 for the next set of measurements.

The sample volumetric fraction portions of Equations (13) are equivalent to $$\dot{f}_{O2\_sample} = \frac{1}{V_{chamber}} \begin{pmatrix} -F_{net\_ambient/patient\_air} f_{O2\_sample} + \\ F_{net\_ambient/patient\_O2} \end{pmatrix}$$

$$\dot{f}_{CO2\_sample} = \frac{1}{V_{chamber}} \begin{pmatrix} -F_{net\_ambient/patient\_air} f_{CO2\_sample} + \\ F_{net\_ambient/patient\_CO2} \end{pmatrix}$$

$$F_{net\_ambient/patient\_O2} = F^*_{ambient} f_{O2\_ambient} - F_{O2\_patient}$$

$$F_{net\_ambient/patient\_CO2} = F^*_{ambient} f_{CO2\_ambient} + F_{CO2\_patient}$$

$$F_{net\_ambient/patient\_air} = F^*_{ambient} - F_{O2\_patient} + F_{CO2\_patient}$$

illustrating their dependence on estimates of the net flow rate of $O_2$ ($F_{net\_ambient/patient\_O2}$) contributed by ambient and the patient, net flow rate of $CO_2$ ($F_{net\_ambient/patient\_CO2}$) contributed by ambient and the patient, and the net flow rate ($F_{net\_ambient/patient\_air}$) of air into the chamber contributed by ambient and the patient.

If $\underline{x}_{i/i}$ is the current best estimate of the state based on measurements taken up to $t_i$, the predicted state at the next measurement time, $t_{i+1}$, is given by integrating the mean values (ignore stochastic terms) of Equations (13) from $t_i$ to $t_{i+1}$ beginning with $\underline{x}_{i/i}$. The integrals are coupled and can be determined using numerical integration or by explicit solutions.

Given the predicted state, $\underline{x}_{i+1/i}$, the measurements are predicted using the mean values of Equations (14) as the two state vector elements, $f_{O2\_sample@i+1/i}$, and $f_{CO2\_sample@i+1/i}$.

Given the predicted measurements, the updated best estimate of the state $\underline{x}_{i+1/i+1}$ is determined by correcting the predicted state using the predicted measurements and the actual measurements as in Equations (12).

Systems theory provides various methods for determining the best kf and kF gains ranging from pole placement through Kalman and H-infinity algorithms. The preferred method is the Kalman filter algorithm as this is straight forward and based on known measurement noise statistics while using the state noise statistics to tune the estimator performance. Optimally, the eight kf and kF gains change with each set of measurements according to the Kalman algorithm, but with reasonable assumptions (e.g. the patient $O_2$ and $CO_2$ flow rates are small compared to the ambient flow, the sample volumetric $O_2$ and $CO_2$ fractions do not change greatly from ambient levels, and $F^*_{ambient}$ is approximately equal to $F_{sample}$), the Kalman algorithm provides a set of fixed kf and kF.

Useful metabolic parameters include $F_{O2\_patient}$ and $F_{CO2\_patient}$ as well as the respiratory quotient, metabolic rate, and others not listed here. Given the patient oxygen and carbon dioxide flow rates, the respiratory quotient (RQ) of the patient is defined as their ratio $$RQ \equiv \frac{F_{CO2\_patient}}{F_{O2\_patient}}$$

RQ provides evidence of the type of metabolism, fat or lipid. Pure carbohydrate metabolism has a RQ of 1.0, and pure lipid metabolism 0.696. Interpolating linearly between these two, the fraction of the metabolism that is carbohydrate ($M_{carbohydrate}$) and that which is lipid ($M_{lipid}$) are $$M_{carbohydrate} = \frac{RQ - 0.696}{1.0 - 0.696}$$

$$M_{lipid} = 1 - M_{carbohydrate}$$

The resulting estimated patient oxygen and carbon dioxide flow rates are referenced to the sample temperature and pressure and need to be re-referenced to standard temperature (273.15° K) and pressure (760 mmHg) using $$F_{x\_patient\_STP} = \frac{273.15 P_{sample}}{760 T_{sample}} F_{x\_patient}$$

and the patient energy expenditure is based (one of many interpretations) on the caloric value of the oxygen consumption at standard conditions: 4.875 kcals/liter of $O_2$ consumed. The energy expenditure (EE), also known as the metabolic rate (MR), is then $$EE = MR$$
$$= 4.875 * F_{O2\_patient\_STP} \text{kcal/second}$$
$$= 4.212 \times 10^5 * F_{O2\_patient\_STP} \text{kcal/day}$$

Figure 3:
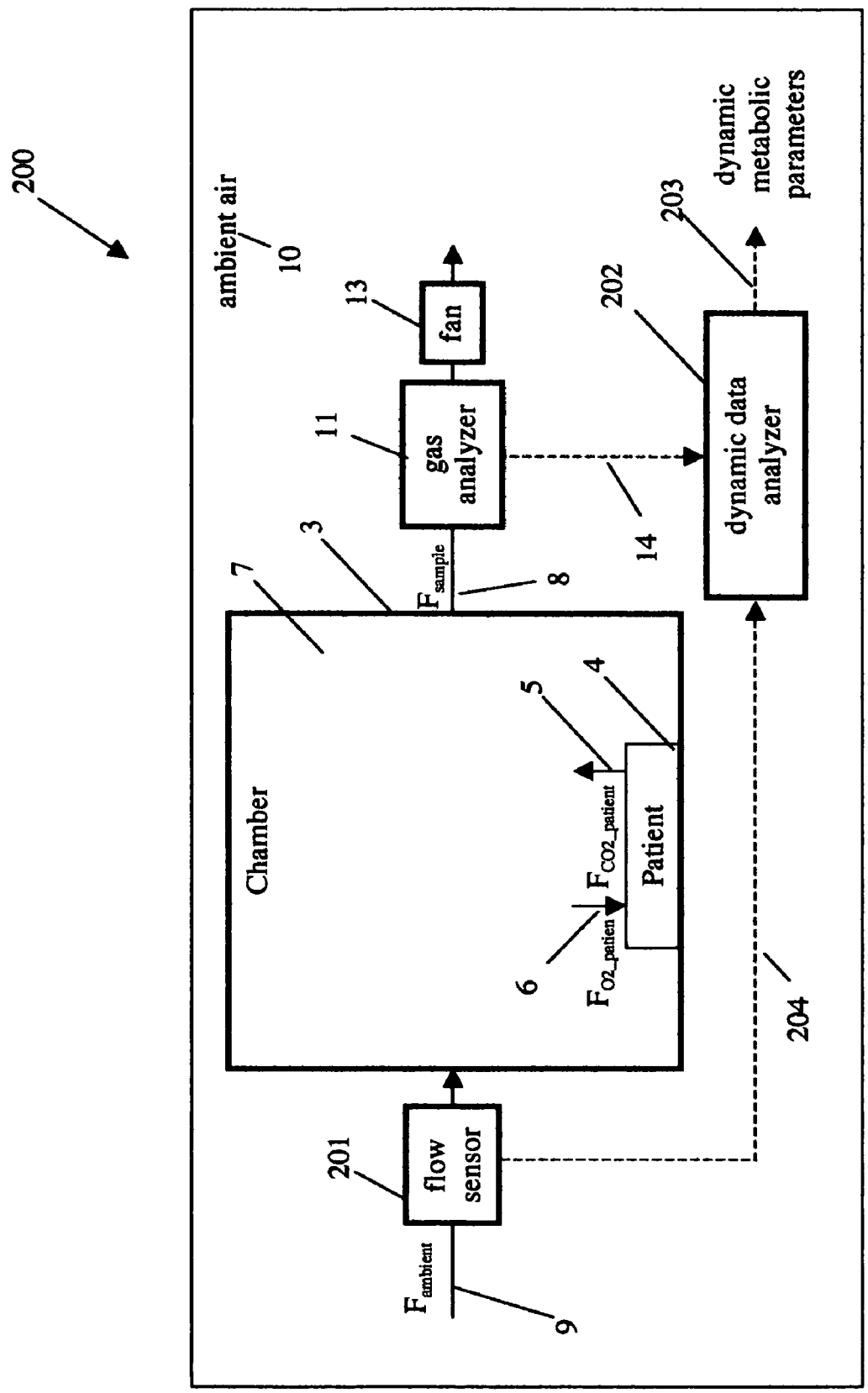
FIG. 3 is a schematic representation of a metabolic chamber using dynamic methods to estimate metabolic parameters.

FIG. 3 illustrates a dynamic metabolic parameter estimation system 200 fitted with an ambient inflow sensor 201 providing inflow rate data 204. The dynamic system 200 uses the dynamic analyzer 202 performing procedure 100, and produces dynamic metabolic parameters 203 based on dynamic estimates of the patient's oxygen consumption rate 6 and carbon dioxide generation rate 5.

Figure 4:
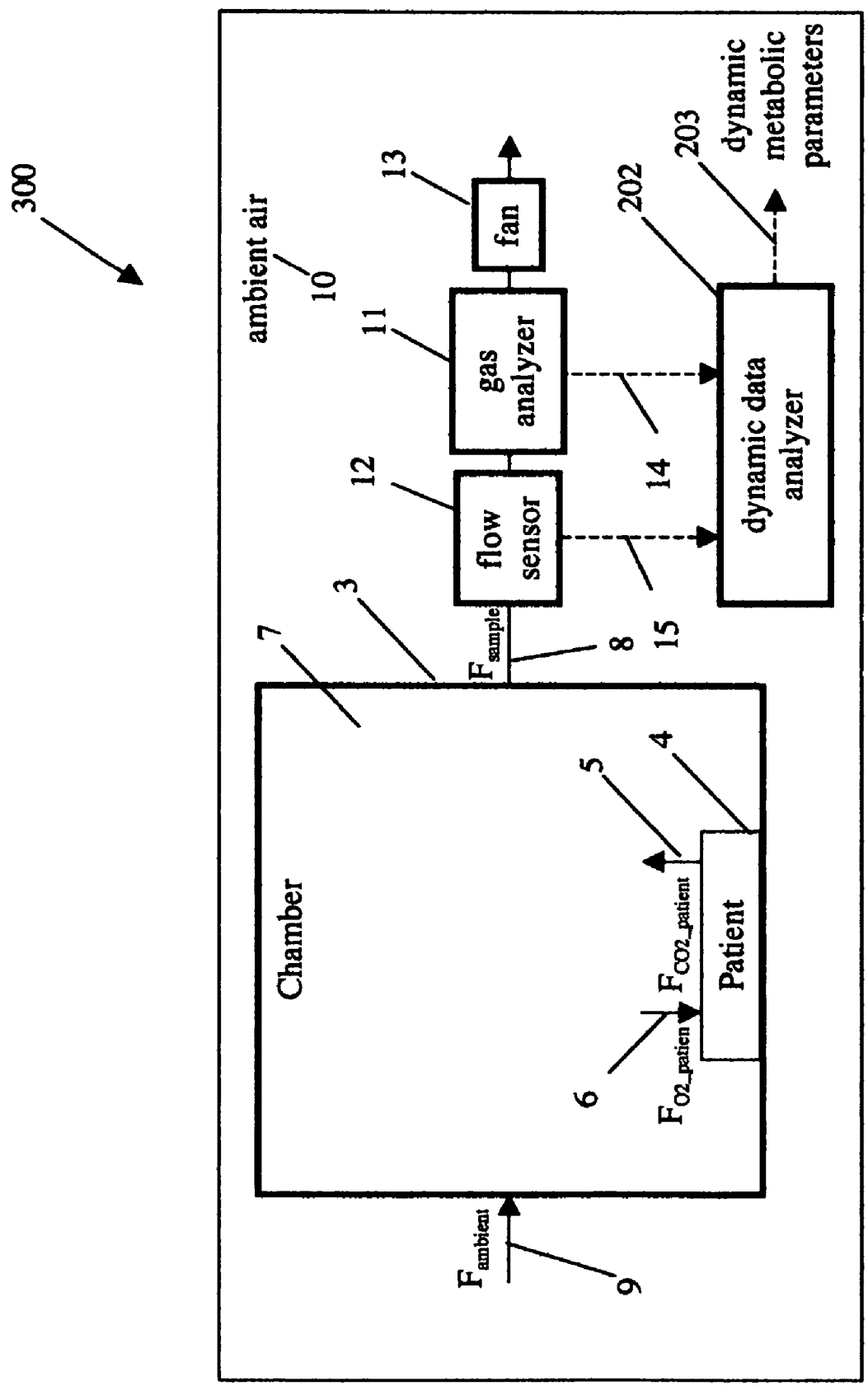
FIG. 4 is a schematic representation of a conventional metabolic chamber retrofitted with a dynamic metabolic parameter estimator.

FIG. 4 illustrates a conventional metabolic parameter estimation system retrofitted 300 with a dynamic analyzer 202 and producing dynamic metabolic parameters 203. A gas outflow sensor 12 and data 15 replace the gas inflow sensor 201 and data 204. This is possible because, under normal operational conditions, the inflow (after pressure, temperature, and humidity compensation) and outflow rates are virtually identical (although inflow lags outflow). In this case the $F^*_{ambient}$ values of Equations (13) are replaced by the gas sampling rate $F_{sample}$.

SIMULATION EXAMPLES

A simulation using Equations (14) is developed of a chamber initially open to ambient that at time zero is closed and the sampling process initiated, and for which
ambient pressure=760 mmHg
ambient and chamber temperatures=22° C.
ambient $O_2$ fraction=0.2095, ambient $CO_2$ fraction=0.0003, $N_2$ fraction=0.7902;
sample flow rate=20 liter/min;
inlet flow resistance=20 mmHg per liter/sec;
chamber volume=500 liters;
measurement errors $\sigma_{fO2\_measurement} = \sigma_{fCO2\_measurement} = 0.00001$ (0.001%);
flow rate measurement standard deviation $\sigma_F = 0.1$ liter/min;
1-second sampling period;
and a patient having
respiratory quotient RQ=0.85;
initial metabolic rate MR=of 450 kcal/day at STP conditions changing to 550 kcal/day after 125 minutes
The resulting data is analyzed using Equations (12-14).

Figure 5:
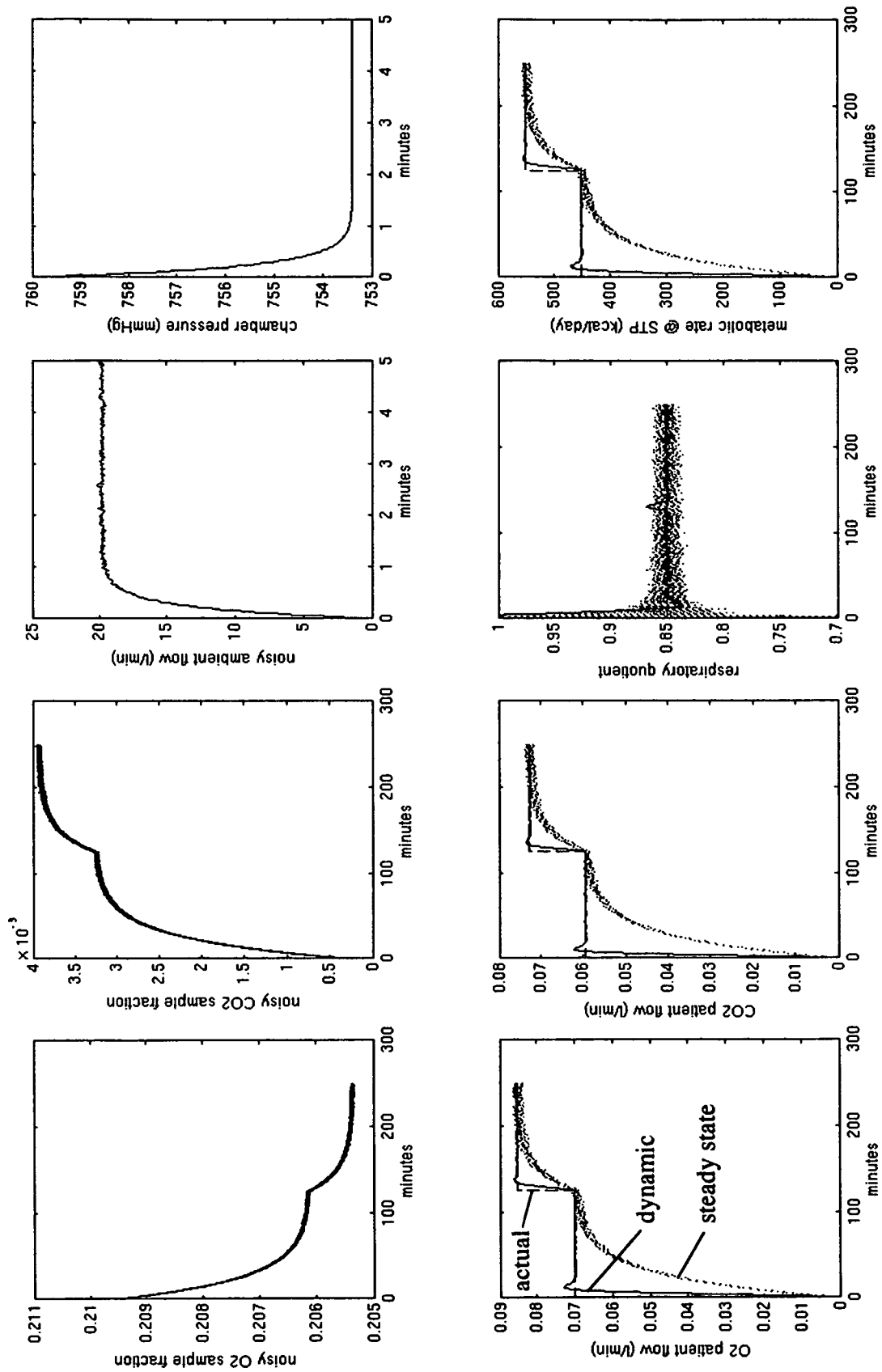
FIG. 5 is a graph comparing the simulated responses of the conventional steady state metabolic parameter estimator with a dynamic estimator having fixed gains where the patient metabolic rate changes.

FIG. 5 shows the chamber response in its upper row of graphs and the estimated metabolic parameters in the lower row as determined using the steady state Equations (10) and also by using a fixed kf and kF gain dynamic estimator of Equations (11-12). The correct solution is shown as a dashed line and, whereas the steady state solution (dotted line) converges in roughly 100 minutes, the dynamic estimator (solid line) converges in roughly 10 minutes: a 10:1 improvement. This suggests the patient can spend ⅒ the time attached to the device. At the same time, the metabolic parameters are estimated with much less variability. As shown, the dynamic estimator responds quickly to the change in metabolic rate (energy expenditure) while the steady state method is waiting for the return of steady state.

Figure 6:
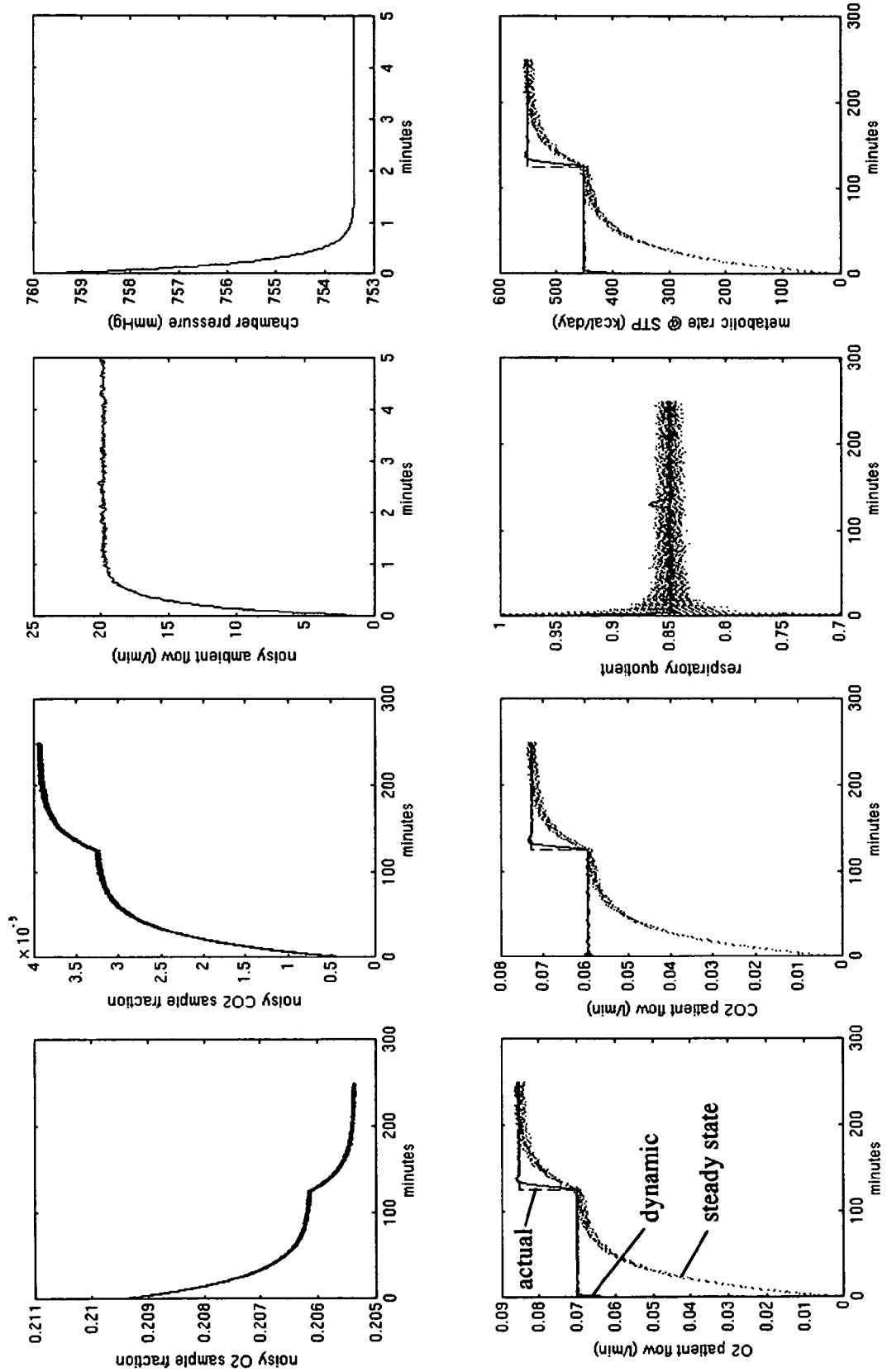
FIG. 6 is a graph comparing the simulated responses of the conventional steady state metabolic parameter estimator with a dynamic estimator having varying gains where the patient metabolic rate changes.

FIG. 6 shows the same simulation but where kf and kF gains change with each measurement according to the Kalman filter algorithm. In this case the dynamic estimator converges in roughly 2 minutes compared to the 100 minutes of the steady state solution: a 50:1 improvement.

Figure 7:
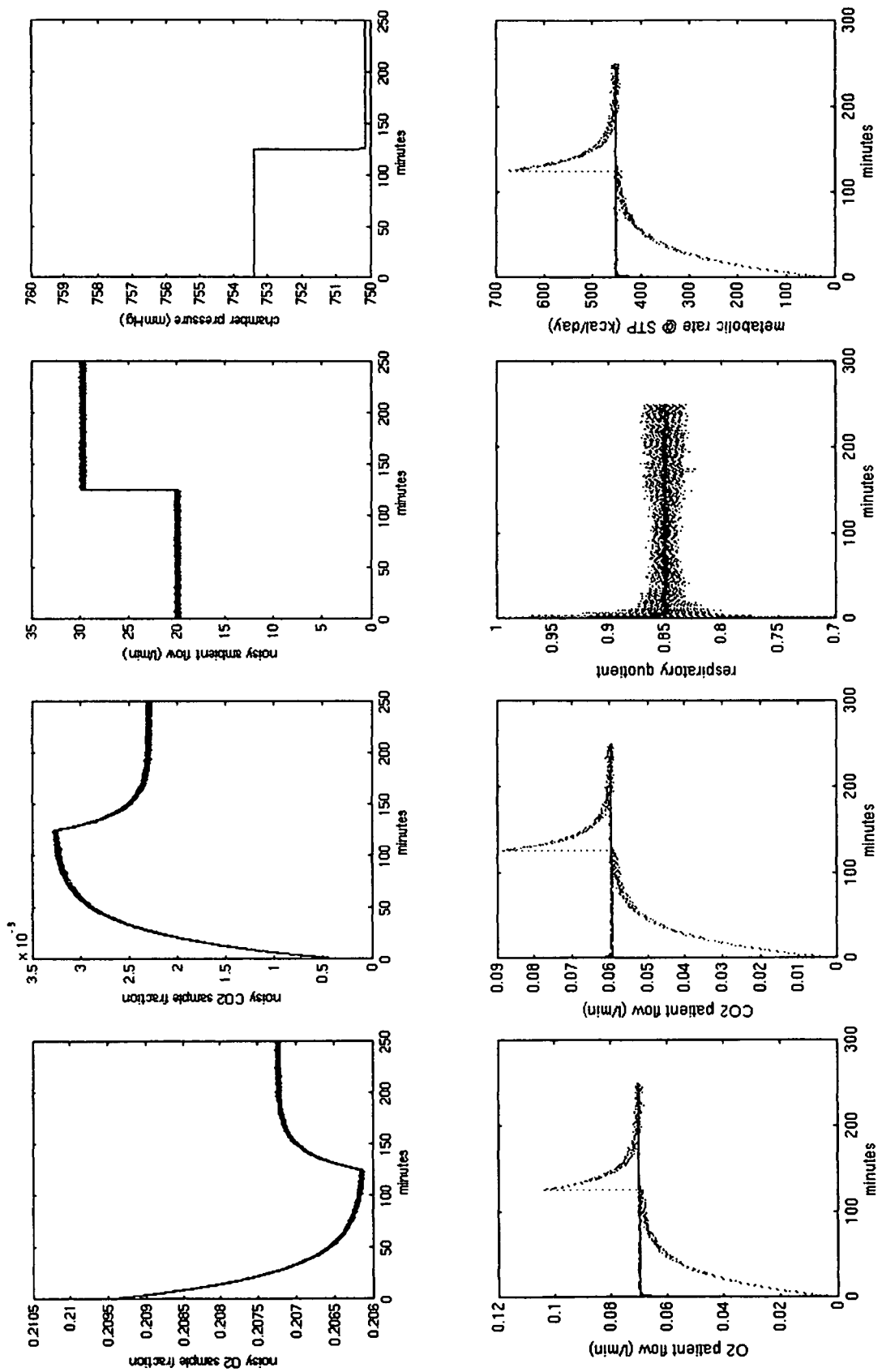
FIG. 7 is a graph comparing the simulated responses of the conventional steady state metabolic parameter estimator with a dynamic estimator having fixed gains where the sample flow rate changes.

FIG. 7 shows the effect of changing sample flow rates: at 125 minutes the sample flow rate is abruptly changed to 30 liter/min with no change in metabolic rate. As shown, the kf and kF fixed gain dynamic estimator is unaffected while the steady state solution is awaiting the return of steady state. A dynamic estimator with changing kf and kF gains is similarly unaffected.

Figure 8:
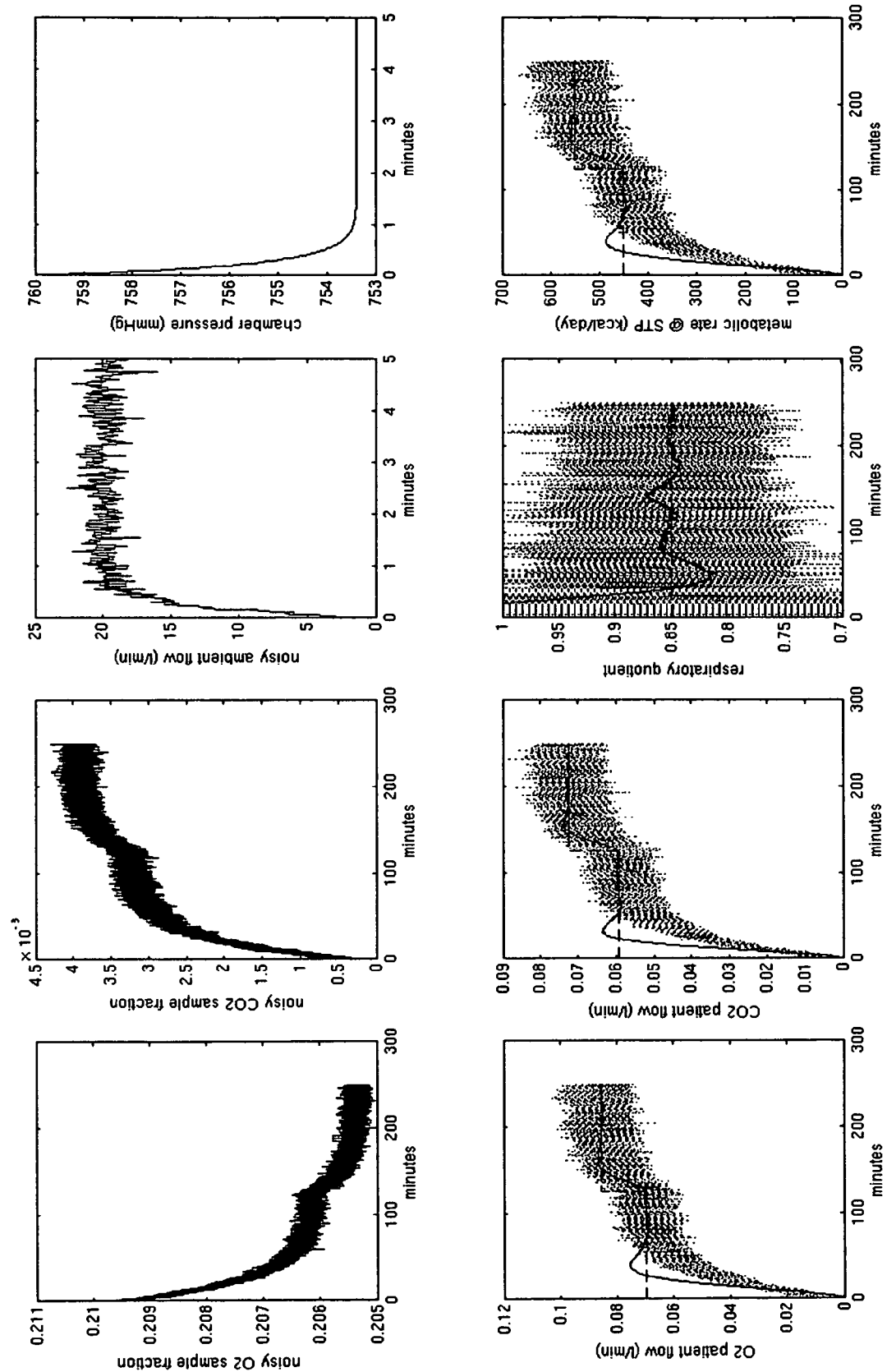
FIG. 8 is a graph comparing the simulated responses of the conventional steady state metabolic parameter estimator with a dynamic estimator having fixed gains where the patient metabolic rate changes and where the measurement instruments have ten times the measurement noise.

FIG. 8 shows the response of the steady state and fixed kf and kF gain dynamic estimator should the measurement instruments be replaced by those with ten times more measurement noise. Although the convergence advantage (it converges in around 50 minutes) of the dynamic estimator is reduced to 2:1, it has much less estimate variability than the steady state.

Figure 9:
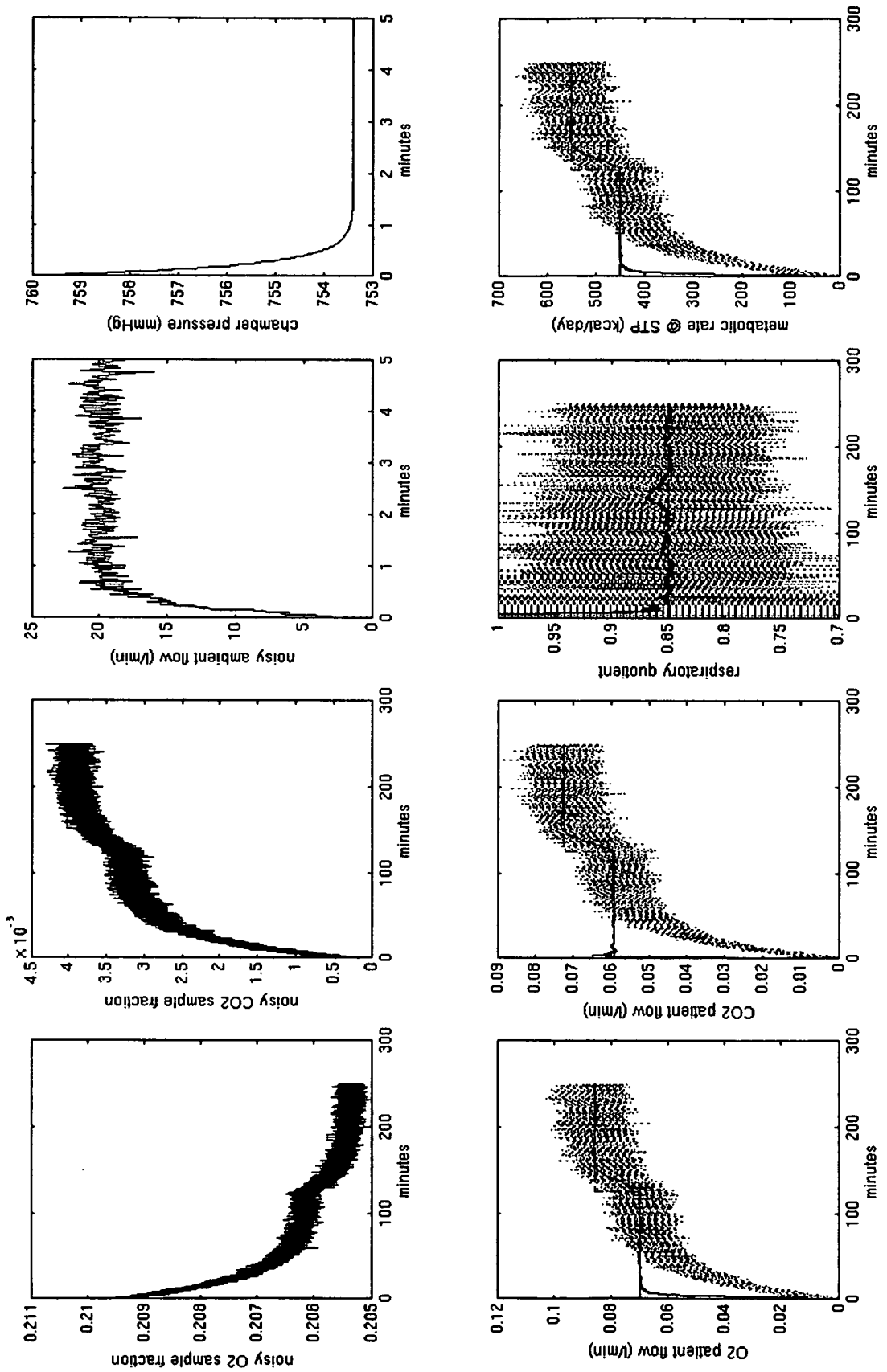
FIG. 9 is a graph comparing the simulated responses of the conventional steady state metabolic parameter estimator with a dynamic estimator having varying gains where the patient metabolic rate changes and where the measurement instruments have ten times the measurement noise.

FIG. 9 shows the less accurate instruments with a variable kf and kF gain dynamic estimator. While its convergence advantage (it converges in around 10 minutes) is reduced to 10:1, it has much less estimate variability than the steady state solution.

Although it is possible to low-pass or window-average the values generated by the steady state method to reduced their variability, this does not eliminate the convergence delay and, since it adds phase, delays convergence even further.

Chamber Volume Determination

Figure 10:
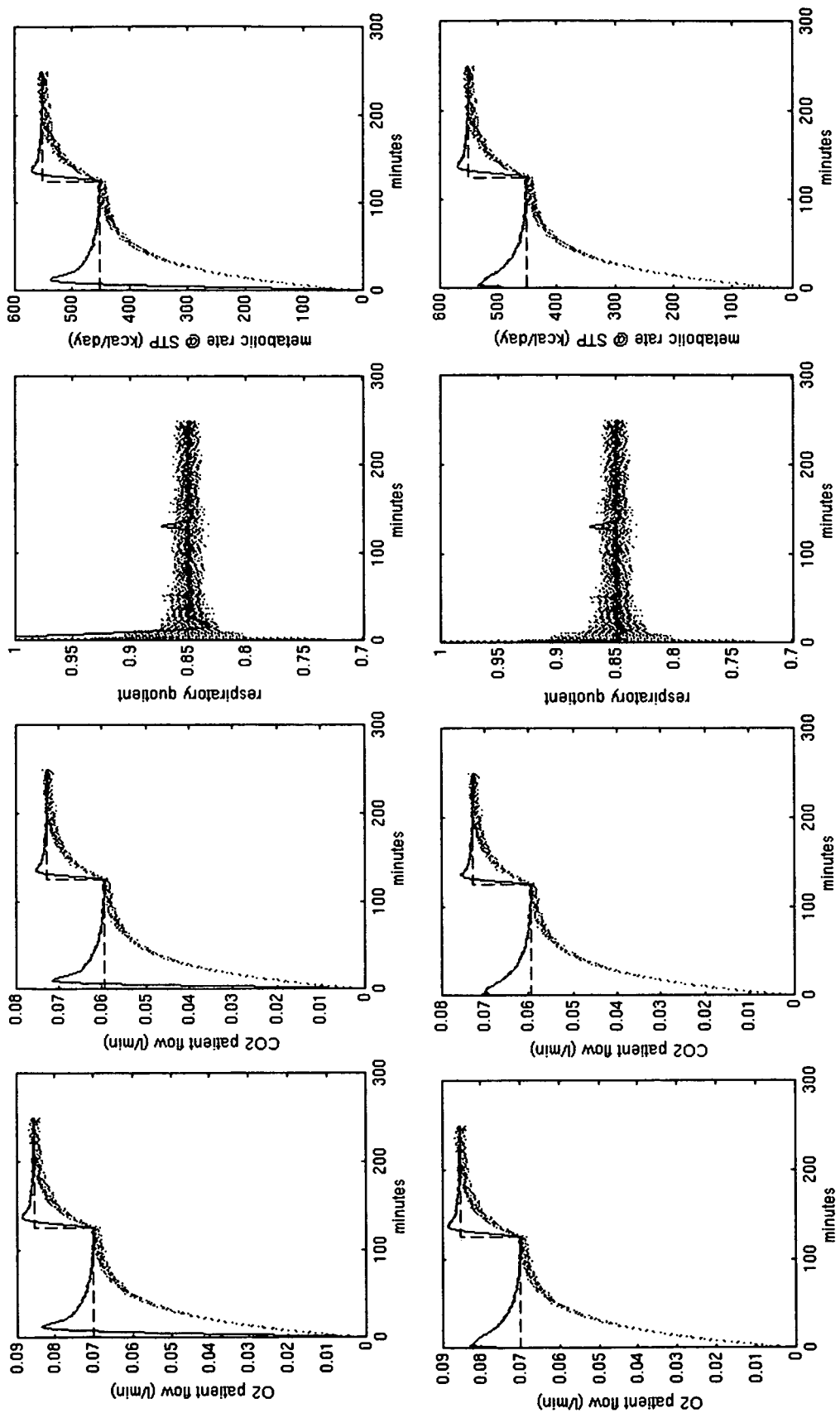
FIG. 10 is a graph illustrating the simulated over-shoot responses of the dynamic estimator having fixed and varying gains where the chamber volume is specified incorrectly 20% to large.
Figure 11:
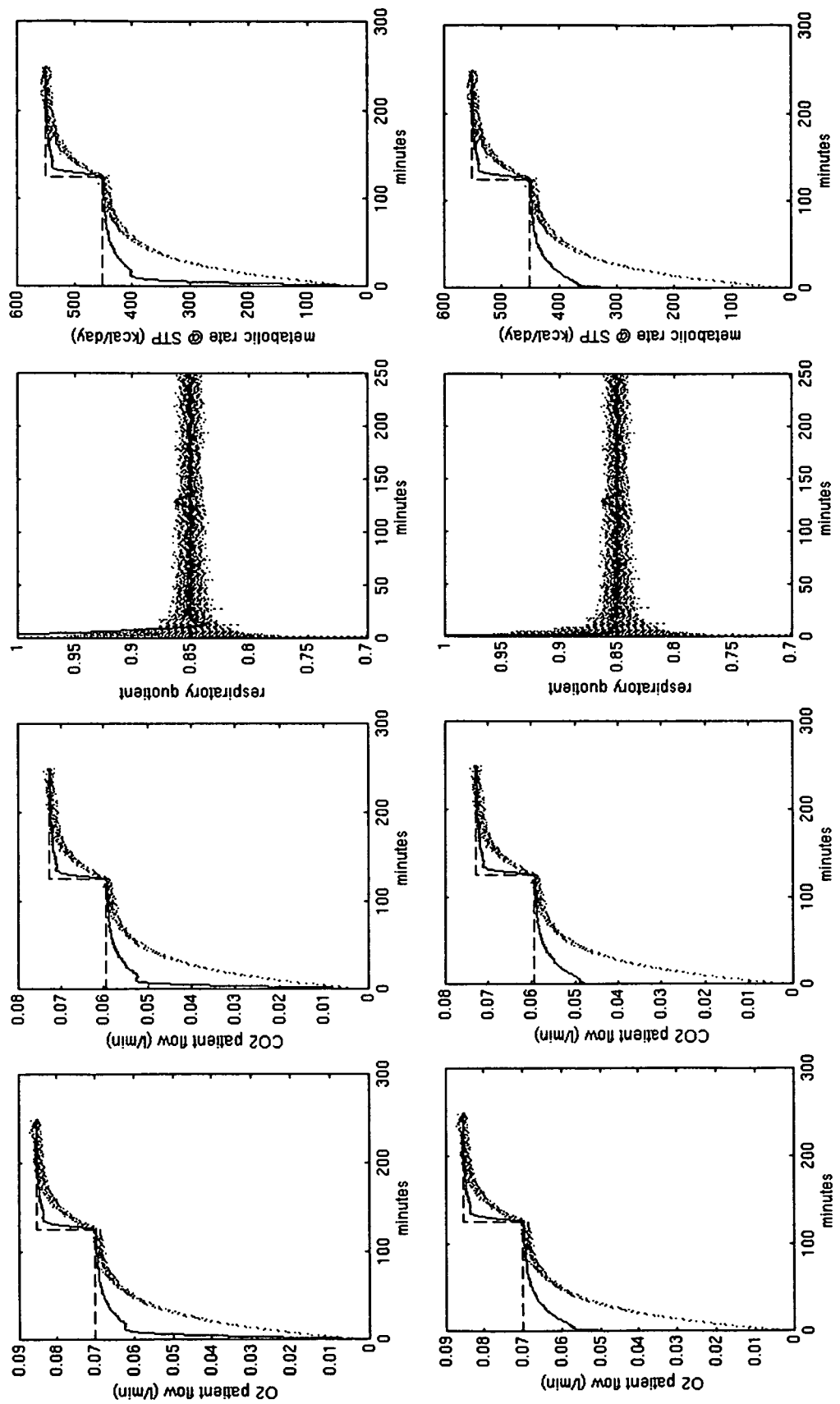
FIG. 11 is a graph illustrating the simulated under-shoot responses of the dynamic estimator having fixed and varying gains where the chamber volume is specified incorrectly 20% too small.

An error in $V_{chamber}$ affects the time response of the dynamic estimator and is corrected by sensing the over- or under-shoot of the $F_{O2\_patient}$ and $F_{CO2\_patient}$ estimates. Too large a $V_{chamber}$ value causes and overshoot, and too small a value causes and undershoot. The effect of a 20% too large value is seen in FIG. 10 where the upper trace is for the fixed gain estimator and the lower trace for the time varying gain estimator. Similarly, FIG. 11 shows the effect of a 20% too small value of $V_{chamber}$. Compared to FIG. 5 and FIG. 6, these show over- and under-shoots respectively, and the amount of over- or under-shoot is used to adjust the value of $V_{chamber}$.

Other Embodiments

While several illustrative embodiments of the invention have been shown and described, numerous variations and alternate embodiments will occur to those skilled in the art. For example, measurements other than volumetric fractions are considered; mathematical models different from those presented are considered; any number of other metabolic parameters is considered; estimators other than Kalman filters are considered; and chambers that full or partially enclose a patient, as well as connect only through a breathing hose, are considered. Such variations and alternate embodiments, as well as others, are contemplated and can be made without departing from the spirit and scope of the invention as defined in the appended claims.

What is claimed is:

1. A metabolism monitor comprising:
   a chamber; said chamber further comprising
      an inlet connected to ambient air to allow said ambient air to enter the chamber,
      an outlet to allow the chamber air to leave the chamber to said ambient air,
      wherein the chamber is further adapted to connect to a respiration of a subject;
   a gas analyzer configured to measure chamber air characteristics;

an air flow sensor connected to the inlet or the outlet to measure chamber air flow; and an estimator including a predictor and a corrector, the estimator configured to initialize values of subject variables and of chamber variables, wherein the subject variables comprise a subject oxygen consumption flow rate and a subject carbon dioxide production flow rate, and the chamber variables comprise chamber air levels of oxygen and of carbon dioxide;

wherein at each of a plurality of times, the monitor:

measures chamber air characteristics, using the gas analyzer, to determine measurement variables, said measurement variables comprising measured chamber air levels of oxygen and of carbon dioxide;

measures chamber air flow, using the air flow sensor, to determine values of the air flow entering the chamber, when the air flow sensor is connected to the inlet, or the values of the air flow exiting the chamber, when the air flow sensor is connected to the outlet;

generates, using the predictor, the values of anticipated subject variables and of anticipated chamber variables in response to values of subject variables, values of chamber variables, and the measured chamber air flow; and corrects, using the corrector, the values of the subject variables and of the chamber variables in response to the values of the measurement variables, the values of the anticipated subject variables, and the values of the anticipated chamber variables; and whereupon a subject metabolism is monitored in response to the values of the corrected subject variables.

2. The monitor of claim 1 further including ambient air and chamber air pressure sensors and where the air flow sensor is responsive to ambient air pressure and chamber air pressure measurements to determine air flow.

3. The monitor of claim 1 where the measurement variables and the chamber variables are in units of volumetric fraction.

4. The monitor of claim 1 where the subject oxygen consumption flow rate and the subject carbon dioxide production flow rate are in terms of volume per unit time.

5. The monitor of claim 1 where the chamber is further adapted to fully enclose the subject.

6. The monitor of claim 1 wherein the estimator further estimates a chamber volume responsive to the plurality of the measurements of chamber air characteristics and the measured chamber air flow.

7. The monitor of claim 1 where the generation of values of anticipated subject variables is responsive to stochastic descriptions of the probable change of said variables at said plurality of times.

8. A method to monitor a metabolism of a subject including the steps of:

connecting, via an inlet, a chamber to ambient air to allow said ambient air to enter the chamber, and, via an outlet, the chamber to ambient air to allow chamber air to leave the chamber to said ambient air, wherein the chamber is further adapted to connect to a respiration of the subject;

providing a gas analyzer configured to measure chamber air characteristics;

providing an air flow sensor connected to the inlet or the outlet and configured to measure chamber air flow; and providing an estimator including a predictor and a corrector, the estimator configured to initialize values of subject variables and of chamber variables, wherein the subject variables comprise a subject oxygen consumption flow rate and a subject carbon dioxide production flow rate, and the chamber variables comprise chamber air levels of oxygen and of carbon dioxide wherein at each of a plurality of times the monitor goes through the steps of:

measuring chamber air characteristics, using the gas analyzer, to determine measurement variables, said measurement variables comprising measured chamber air levels of oxygen and of carbon dioxide;

measuring chamber air flow, using the air flow sensor, to determine values of the air flow entering the chamber, when the air flow sensor is connected to the inlet, or the values of the air flow exiting the chamber, when the air flow sensor is connected to the outlet;

generating, using the predictor, the values of anticipated subject variables and of anticipated chamber variables in response to values of subject variables, values of chamber variables, and the measured chamber air flow; and correcting, using the corrector, the values of the subject variables and of the chamber variables in response to the values of the measurement variables, the values of the anticipated subject variables, and the values of the anticipated chamber variables; and whereupon a subject metabolism is monitored in response to the values of the corrected subject variables.

9. The method of claim 8 further providing ambient air and chamber air pressure sensors and where the air flow sensor is responsive to ambient air pressure and chamber air pressure measurements to determine air flow.

10. The method of claim 8 where the measurement variables and the chamber variables are in units of volumetric fraction.

11. The method of claim 8 where the subject oxygen consumption flow rate and the subject carbon dioxide production flow rate are in terms of volume per unit time.

12. The method of claim 8 where the chamber is further adapted to fully enclose the subject.

13. The method of claim 8 wherein the estimator further estimates a chamber volume responsive to the plurality of the measurements of chamber air characteristics and the measured chamber air flow.

14. The method of claim 8 where the generation of values of anticipated subject variables is responsive to stochastic descriptions of the probable change of said variables at said plurality of times.

* * * * *

UNITED STATES PATENT AND TRADEMARK OFFICE
CERTIFICATE OF CORRECTION

| | | |
|---|---|---|
| PATENT NO. | : 8,109,884 B2 | Page 1 of 1 |
| APPLICATION NO. | : 11/525803 | |
| DATED | : February 7, 2012 | |
| INVENTOR(S) | : Kitchener Clark Wilson | |

It is certified that error appears in the above-identified patent and that said Letters Patent is hereby corrected as shown below:

Column 3, Line 47 of the specification is a portion of an equation for qdot_CO2_chamber that ends on that line as "qdot_CO2_sample -." should read -- qdot_CO2_sample + --

Signed and Sealed this
Twenty-seventh Day of March, 2012

David J. Kappos
*Director of the United States Patent and Trademark Office*